(12) United States Patent
Sigman et al.

(10) Patent No.: US 8,706,426 B2
(45) Date of Patent: Apr. 22, 2014

(54) SYSTEMS AND METHODS FOR IDENTIFYING CLASSES OF SUBSTANCES

(75) Inventors: Michael Sigman, Oviedo, FL (US); Mary Williams, Eustis, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 523 days.

(21) Appl. No.: 13/088,980

(22) Filed: Apr. 18, 2011

(65) Prior Publication Data

US 2011/0270535 A1    Nov. 3, 2011

Related U.S. Application Data

(60) Provisional application No. 61/324,932, filed on Apr. 16, 2010.

(51) Int. Cl.
*G01N 31/00* (2006.01)
(52) U.S. Cl.
CPC ..................................... *G01N 31/00* (2013.01)
USPC .......................................................... 702/28
(58) Field of Classification Search
USPC ................................... 702/28, 130, 182–185
See application file for complete search history.

(56) References Cited

U.S. PATENT DOCUMENTS

| | | | |
|---|---|---|---|
| 2,400,557 A | 7/1942 | Lawlor | |
| 5,498,875 A | 3/1996 | Obremski | |
| 6,444,979 B1 | 9/2002 | Watanabe | |
| 6,913,930 B2 | 7/2005 | Bevan | |
| 7,002,143 B2 | 2/2006 | Parker | |
| 7,022,980 B2 | 4/2006 | Zavitsanos | |
| 7,072,770 B1 | 7/2006 | Schweitzer | |
| 7,425,700 B2 | 9/2008 | Stults | |
| 2004/0126892 A1 | 7/2004 | Bogomolov | |
| 2007/0127022 A1 | 6/2007 | Cohen | |
| 2008/0015352 A1 | 1/2008 | Piccarello | |
| 2008/0262321 A1* | 10/2008 | Erad et al. | 600/301 |
| 2009/0012723 A1 | 1/2009 | Treado | |

FOREIGN PATENT DOCUMENTS

GB          2410800          10/2005

OTHER PUBLICATIONS

Gan, et al., "A Novel Approach to the Retrieval of the Mass Spectrum", Analytical Sciences, Jun. 2000, vol. 16, pp. 603-607.
Hallgren, et al. "Quantitative Mass Spectrometric Analysis of Mixtures of Unsaturated and Saturated Fatty Acids", Short Communications; Department of Medical Biochemistry, Institute of Medical Chemistry, University of Uppsala., Acta Chem, Scand. 11 (1957) No. 6, pp. 1064-1065.
Yates, "Database searching using mass spectrometry data", Protein identification using mass spectrometry, Electrophoresis 1998, 19, pp. 893-900, Dept. of Molecular Biotechnology, School of Medicine, University of Washington, Seattle, WA.

(Continued)

*Primary Examiner* — Edward Raymond
(74) *Attorney, Agent, or Firm* — Dunlap Codding P.C.

(57) ABSTRACT

In one embodiment, a system and a method for identifying the class of a component of a mixture includes collecting samples from a sample source, determining a summed ion spectrum for each sample and generating sample data from the summed ion spectra, comparing the sample data with reference summed ion spectra of multiple reference substances to determine correlations between the reference substances and the sample data, and evaluating the correlations of the substances of each substance class to determine which substance class most closely correlates to the sample data.

29 Claims, 5 Drawing Sheets

(56) References Cited

OTHER PUBLICATIONS

Zarrabi, et al. "Use of principal component regression to characterize a complex oxidation product mixture", Dept. of Chemistry and Ceochemistry, Colorado School of Mines, Golden, CO, 1991 Elsevier Science Publishers, pp. 1-285.

Kang, et al. "Decomposition of multicomponent mass spectra using Bayesian probability theory", Centre for Interdisciplinary Plasma Science, Sep. 18, 2002, pp. 1-18.

Geert Van Marlen, et al., "Information Theory Applied to Selection of Peaks for Retrieval of Mass Spectra", ACS Publications, Analytical Chemistry, May 1, 2002, pp. 594-598.

Stanley L. Grotch, "Matching of Mass Spectra When Peak Height is Encoded to One Bit", ACS Publications, Analytical Chemistry, May 1, 2002, pp. 1213-1222.

Sigman, et al., "Ignitable Liquid Classification and Identification using the Summed-Ion Mass Spectrum", Instrumentation Science and Technology, 36: 375-393, 2008.

Gonzalez-Arjona, et al., "Performing procrustes discriminant analysis with Holmes", 1999 Elsevier Science, p. 189-197.

Sigman, et al. "Individualization of Gasoline Samples by Covariance Mapping Gas . . . ", Dept of Chem and Nat Center for Forensic Science, UCF, vol. 79, No. 9, 5-1-07, 3462-3468.

Sigman, et al., "Covariance Mapping in the Analysis of Ignitable . . . ", Dept of Chem and National Center for Forensic Science, UCF, vol. 78, No. 5, 3-1-26, pp. 1713-1718.

\* cited by examiner

SYSTEMS AND METHODS FOR IDENTIFYING CLASSES OF SUBSTANCES

CROSS-REFERENCE TO RELATED APPLICATION

This application claims priority to co-pending U.S. provisional application entitled, "Classification of a Complex Mixture, or Components of a Complex Mixture, by Combining Target Factor Analysis with a Bayesian Classifier," having Ser. No. 61/324,932, filed Apr. 16, 2011, which is entirely incorporated herein by reference.

STATEMENT REGARDING FEDERALLY-SPONSORED RESEARCH OR DEVELOPMENT

This invention was made with Government support under Contract/Grant No. NIJ Award #2008DNBXK069, awarded by the National Institute of Justice. The Government has certain rights in this invention.

BACKGROUND

It is often necessary to analyze mixtures to determine what components they contain. This is true, for example, in the field of forensic science. Specifically, a forensic scientist may be called upon to analyze a sample from the scene of a fire or an explosion that occurred. In the case of a fire, the scientist may need to determine if an ignitable liquid is present in a fire debris sample. In the case of an explosion, the scientist may need to identify explosive materials that were used to cause the explosion.

There are various methods for identifying a particular chemical compound in a mixture often by separation of the chemicals prior to identification. In other cases, however, it is necessary to identify the class to which a particular combination of chemicals pertains. For example, it may be desired to determine what class of ignitable liquid (e.g., gasoline, normal alkane, etc.) is present in a fire debris sample. In this example, gasoline is comprised of a combination of individual chemicals, and that combination of chemicals constitutes a component of the mixture. The mixture contains the component and additional chemicals that may comprise other components. Existing identification methods are not designed to make such component classifications in complex mixtures. It can therefore be appreciated that it would be desirable to have an effective system and method for classifying a component of a mixture.

BRIEF DESCRIPTION OF THE FIGURES

The items in the drawings are not necessarily to scale, emphasis instead being placed upon clearly illustrating the principles of the present disclosure. In the drawings, like reference numerals designate corresponding parts throughout the several views.

DETAILED DESCRIPTION

As described above, it would be desirable to have an effective system and method for classifying a component of a mixture. Disclosed herein are such systems and methods. In some embodiments, samples are collected and summed ion spectra are generated for each sample. Principal components analysis is performed on the sample data to determine the number of components required to reproduce the variance in the data to a desired level and thereby reduce the dimensionality of the data. Target factor analysis is performed on the dimensionally-reduced data by comparing test vectors (reference summed ion spectra) from a reference library and the correlation between each test vector and the dimensionally-reduced data is calculated. The top class match or matches can be then be identified by evaluating the distributions of correlations for each class using Bayesian decision theory.

Described in the following are various embodiments of systems and methods for identifying classes of substances (components) contained in materials (mixtures). Although particular embodiments are described, those embodiments are mere example implementations of the systems and methods and it is noted that other embodiments are possible. All such embodiments are intended to fall within the scope of this disclosure.

Figure 1:
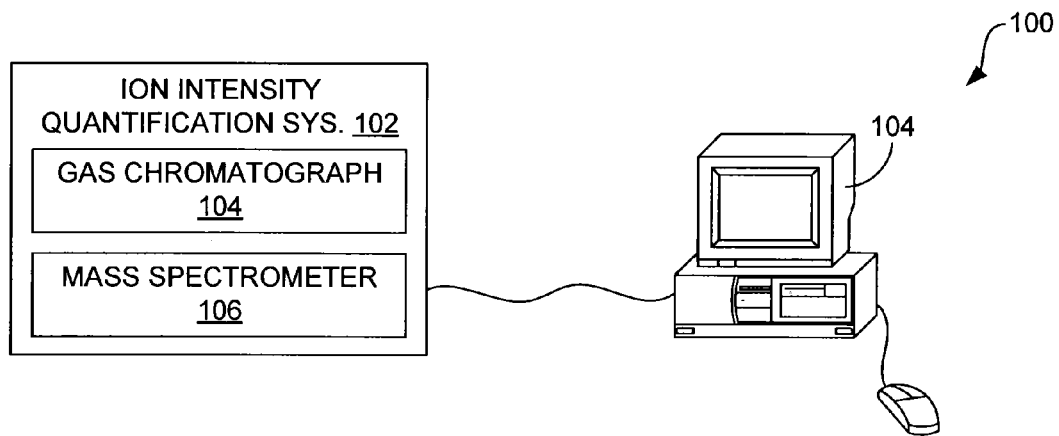
FIG. 1 is a block diagram of an embodiment of a system for identifying a class of a component of a mixture.

FIG. 1 illustrates an example system 100 with which materials can be analyzed to identify classes of substances, such as ignitable liquids or explosive materials, contained in the samples. As indicated in FIG. 1, the system 100 generally comprises an ion intensity quantification system 102 and a computer 104 that are coupled such that data can be sent from the data collection system to the computer. By way of example, the system 100 comprises part of a network, such as a local area network (LAN) or wide area network (WAN).

As its name suggests, the ion intensity quantification system 102 is configured to quantify the ion intensity of ions resulting from compounds, such as those contained in test samples. In the illustrated embodiment, the ion intensity quantification system 102 comprises a gas chromatograph 104 and a mass spectrometer 106 that together break the components of a given mixture down into various ions. Notably, the gas chromatograph and the mass spectrometer can be combined into a single apparatus (i.e., a GC/MS). Of course, other equipment could be used. For instance, laser spectroscopy could be performed instead of gas chromatography.

As described below, the computer 104, and more particularly software provided on the computer, is configured to receive the ion intensity information from the ion intensity quantification system 102 and identify classes of substances (e.g., ignitable liquids, explosive materials) that may be contained in the sample.

Figure 2:
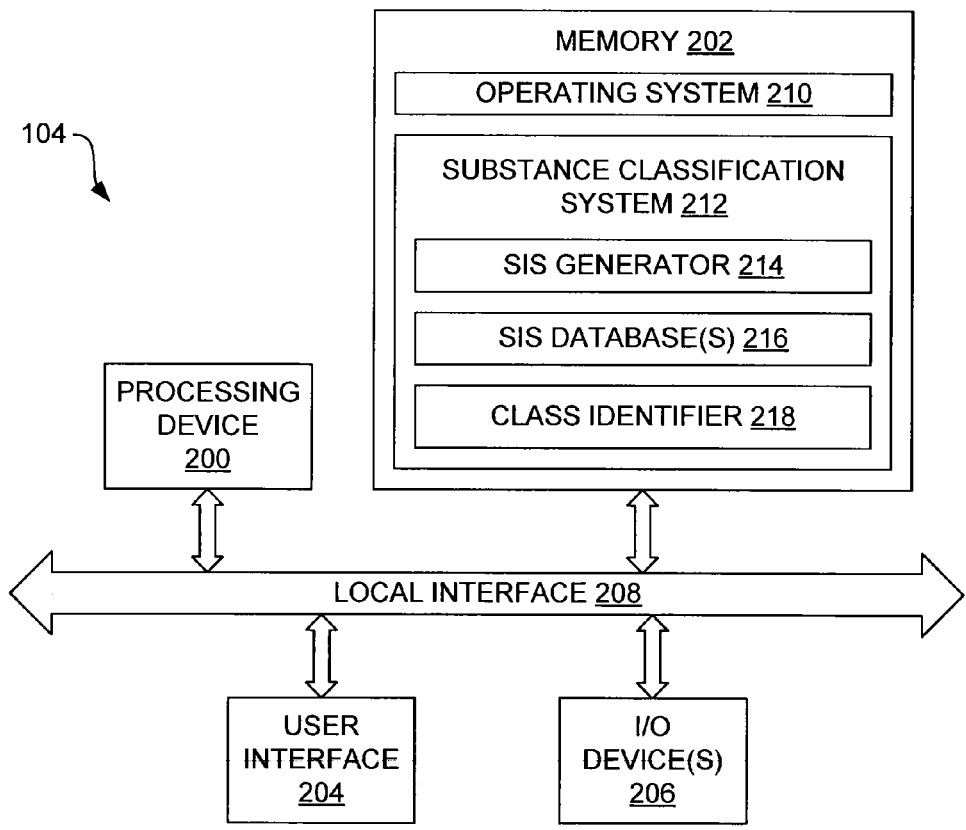
FIG. 2 is a block diagram of an embodiment of a computer shown in FIG. 1.

FIG. 2 is a block diagram illustrating an example architecture for the computer 104 shown in FIG. 1. The computer 104 of FIG. 2 comprises a processing device 200, memory 202, a user interface 204, and at least one I/O device 206, each of which is connected to a local interface 208.

The processing device 200 can include a central processing unit (CPU) or a semiconductor-based microprocessor in the form of a microchip. The memory 202 includes any one of a combination of volatile memory elements (e.g., RAM) and nonvolatile memory elements (e.g., hard disk, ROM, etc.).

The user interface 204 comprises the components with which a user interacts with the computer 104 and therefore may comprise, for example, a keyboard, mouse, and a display. The one or more I/O devices 206 are adapted to facilitate communications with other devices or systems and may include one or more communication components such as a modulator/demodulator (e.g., modem), wireless (e.g., radio frequency (RF)) transceiver, network card, etc.

The memory 202 (i.e., a computer-readable medium) comprises various software programs including an operating system 210 and a substance classification system 212. The operating system 210 controls the execution of other programs and provides scheduling, input-output control, file and data management, memory management, and communication control and related services. As is indicated in FIG. 2, the substance classification system 212 comprises various modules, including a summed ion spectrum generator 214, one or more summed ion spectra libraries 216, and a class identifier 218. Although each of those components are illustrated as being contained within in a single system 212 and stored on a single computer, it is noted that the components can be separated and/or distributed over two or more computers.

The summed ion spectrum generator 214 is configured to sum the ion intensities identified by the ion intensity quantification system 102 for all components of test samples.

The one or more summed ion libraries 216 comprise summed ion spectra for various substances, such as ignitable liquids and explosive materials. Each substance is associated with a given class of substances. For instance, if the substances are ignitable liquids, each is associated a particular class of ignitable liquids, such as aromatic (AR), gasoline, isoparaffinic (ISO), miscellaneous (MISC), normal alkane (NA), naphthenic paraffinic (NP), oxygenate (OXY), and petroleum distillate (PD). The stored spectra can be grouped according to the class to which they pertain, or the spectra can be tagged as pertaining to a particular class. In some embodiments, the libraries 216 can be stored on a separate computer that can be accessed using a network, such as the Internet. For example, the libraries 216 can comprise central libraries hosted by an official governing body (e.g., U.S. government) from which spectra can be downloaded by analysts for the purpose of comparison with collected samples.

The class identifier 218 is configured to compare the summed ion spectra contained in the libraries 216 with data associated with the summed ion spectra of collected samples to determine the correlations between them and, ultimately, the class or classes to which a substance contained in the samples might pertain.

Various programs (i.e. logic) have been described herein. Those programs can be stored on any computer-readable medium for use by or in connection with any computer-related system or method. In the context of this document, a computer-readable medium is an electronic, magnetic, optical, or other physical device or means that contains or stores a computer program for use by or in connection with a computer-related system or method. Those programs can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In view of the consistency of the mass spectra that are generated for given components, particularly when performing electron ionization at 70 electron-volts (eV), and therefore the uniqueness of the ratios of ions produced for such components, unique combinations of components, for example contained in substances from a collected sample, likewise exhibit unique ratios of ions. Therefore, the summed ion spectrum can provide a unique "fingerprint" or "signature" of the sample that can be compared with the summed ion spectra of other substances to identify one or more classes of substances contained in the test sample with a relatively high degree of accuracy.

Figure 3:
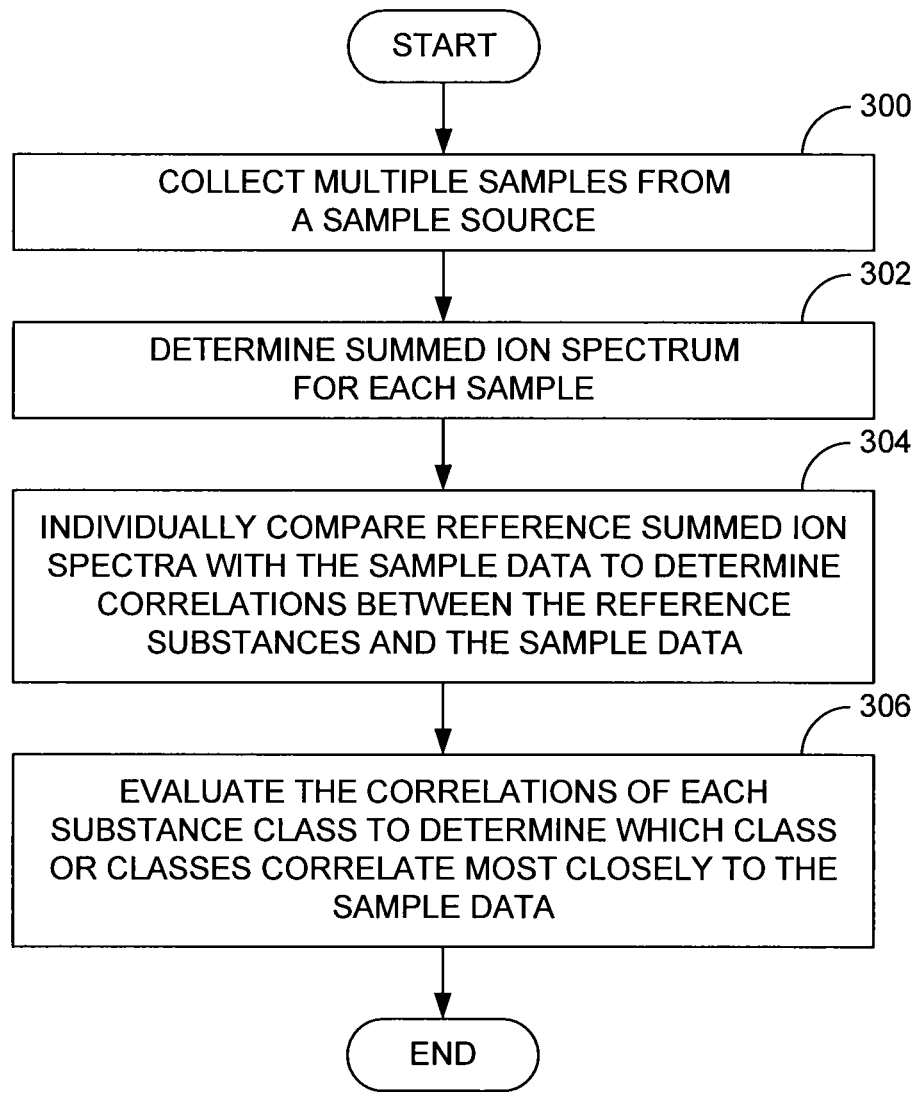
FIG. 3 is a flow diagram of a first embodiment of a method for identifying a class of a component of a mixture.

FIG. 3 provides an overview of an example method for identifying the class of a substance (component) contained in a material (mixture) using summed ion spectra. Beginning with block 300, multiple samples that are to be evaluated are collected from a sample source. Assuming for purposes of discussion that the evaluation is to be performed in relation to the scene of a fire, the samples can be debris samples collected from various locations at the fire scene. By way of example, 5-15 (e.g., 10) such samples can be collected. Notably, each sample may have different concentrations of a substance (e.g., ignitable liquid) that was used to start the fire as well as background substances (e.g., furniture, carpet, etc.) that were burned in the fire. This produces a variance of concentration across the samples.

Figure 4:
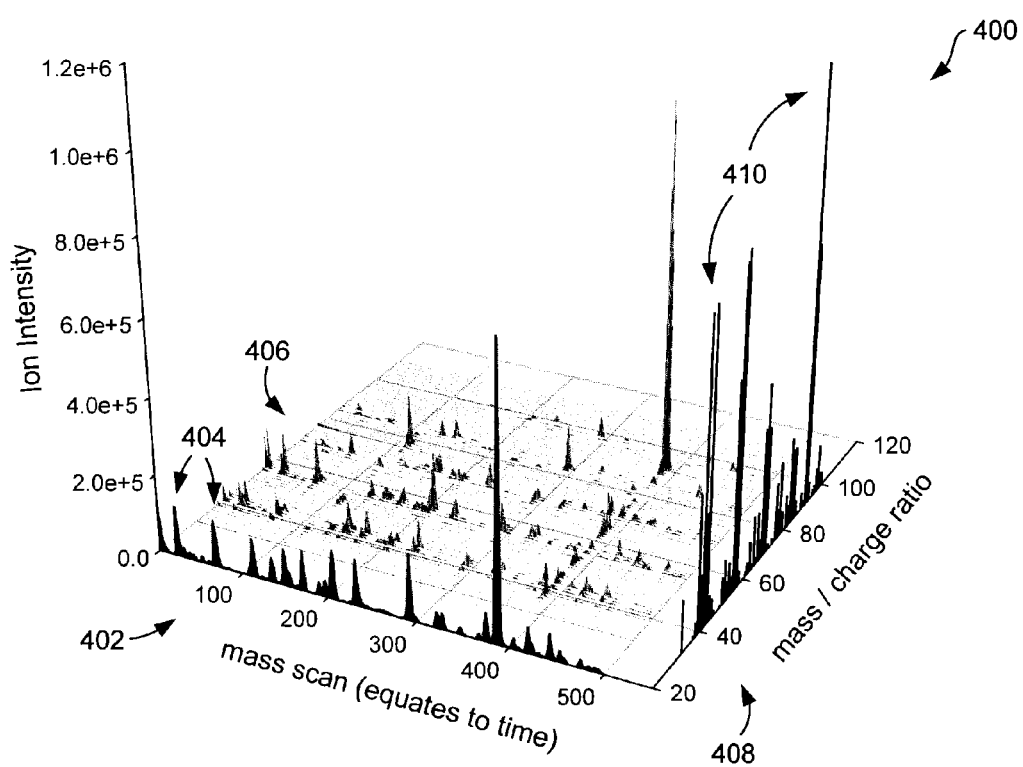
FIG. 4 is a three-dimensional graph that comprises various information regarding an analyzed sample, including the sample's total ion chromatogram, mass spectrum, and summed ion spectrum.

Turning next to block 302, the summed ion spectrum can be determined for each sample. One method for determining summed ion spectra is described in U.S. patent application Ser. No. 12/244,281, which is hereby incorporated by reference in its entirety into this disclosure. As described in that application, the various components of the sample can be separated using a gas chromatograph. During the separation, the various compounds contained within the sample elute at different times, resulting in a total ion chromatogram that plots the total detector response from ions detected as a function of time. The three-dimensional graph 400 of FIG. 4 illustrates an example of a total ion chromatogram 402. As indicated in that figure, the total ion chromatogram 402 comprises multiple peaks 404, each pertaining to a different component (and its ions) that has been separated from the sample at a particular point in time.

The ion intensities from each of the components of the samples can be determined relative to their mass-to-charge ratios. In that process, the ions of each peak 404 of the total ion chromatogram 402 are analyzed to obtain an indication or representation of the number of ions for each of multiple mass-to-charge ratios. The ion intensities are identified as a function of mass-to-charge ratios in the graph 400 of FIG. 4 as a data set 406 (i.e., the peaks in the center of the x-y plane of the graph). In some embodiments, the ion intensities are determined using a mass spectrometer. In such a case, the various components can be received (e.g., from the gas chromatograph) by an ion source of the mass spectrometer that strips electrons from the component molecules to form positive ions, which then break down into molecular fragments. The fragments that have a positive charge are then accelerated out from the ion source through a mass analyzer of the mass spectrometer, and into a detector that identifies ion intensities as a function of their mass-to-charge ratios.

The total ion intensity, which is proportional to the number of ions counted as for each chemical compound, can be totaled to yield a spectrum of ion intensities as a function of their mass-to-charge ratios. The graph 400 of FIG. 4 illustrates an example summed ion spectrum 408, which comprises multiple peaks 410 that pertain to various different mass-to-charge ratios between 30 and 100. Each peak 410 represents the total number of ions that have the various mass-to-charge ratios identified along the axis of the spectrum 408. For example, the tallest peak 410 in the summed ion spectrum 408 appears for ions having a mass-to-charge ratio of 91, thereby indicating that there were a greater number of ions having a mass-to-charge ratio of 91 in the sample than any other mass-to-charge ratio. Given that the charge of each ion is +1, the summed ion spectrum 408 may be considered to provide an indication of the total number of ions grouped according to their respective masses.

The summed ion spectrum can be normalized, if desired, to create a normalized sum ion spectrum. In some embodiments, normalization comprises dividing the intensity for each ion in the summed ion spectrum by the total intensity of all ions in the spectrum. In other embodiments, normalizing can be performed by dividing the ion intensities by the highest ion intensity. Regardless of the method used, normalizing facilitates comparison of the summed ion spectra with other summed ion spectra.

Once the summed ion spectra have been determined, sample data results that can be compared with reference summed ion spectra of multiple substances contained within a reference library. In keeping with the fire scene example, the library can comprise summed ion spectra for hundreds of ignitable liquids that belong to various ignitable liquid classes. As indicated in block 304 of FIG. 3, the reference summed ion spectra are individually compared with the sample data to determine a correlation between each reference substance and the sample data. As is described in greater detail below, the dimensionality of the sample data set can be reduced using target factor analysis (TFA) to simplify the comparison process.

After the comparisons have been performed, the correlations of the substances in each substance class (e.g., ignitable liquid class) can be evaluated to determine which class or classes correlate most closely to the sample data, as indicated in block 306. As is described in greater detail below, this classification can be performed using Bayesian decision theory using a soft classifier.

As mentioned above, the summed ion spectra from the samples together form a sample data set. The summed ion spectra can be compiled as a data matrix that can be compared to the reference data. Because the data matrix contains data that relates to background materials in the samples that is not needed to perform the substance classification, the dimensionality of the data can be reduced and the comparison process can be simplified. This dimensionality reduction and classification can be achieved by performing the steps of target factor analysis. Principal components analysis (PCA) can be performed as a first step of the target factor analysis to obtain a set of latent variables that can be used to identify potential matches. As indicated in Equation 1, the data matrix can be factored into a product of two matrices $[R^{\ddagger}]$ and $[C^{\ddagger}]$, which are the scores matrix and loadings matrix, respectively. Those matrices are designated by the $\ddagger$ superscript to indicate that the matrices retain only the number of principal components required to reproduce the desired fraction of the variance in the data. The number of principal components retained may be estimated by several methods, including screen plots, the rule of one, or the determination of rank by median absolute deviation (DRMAD) method.

$$[D]=[R^{\ddagger}][C^{\ddagger}] \quad (1)$$

The data matrix [D] is an (n×m) matrix comprising n samples (i.e., spectra) measured at m variables (i.e., wavelengths, mass:charge ratios, etc.). The factors in matrix $[C^{\ddagger}]$ are comprised of an ortho-normal set of eigenvectors that represent abstract mathematical solutions to the problem and do not represent physically meaningful variable collections (i.e., spectra of the chemical species that contribute to [D]). The components of $[C^{\ddagger}]$ may contain negative values and represent contributions from the analyte (substance) of interest (e.g., ignitable liquid) as well as contributions from background material.

In order to identify variable sets that are physically meaningful (i.e., real spectra) and those that can regenerate the original data without introducing significant error, the orthogonal factors are transformed through oblique rotations. This can be expressed mathematically as in Equation 2 where [T] is the transformation matrix that brings about the oblique rotations.

$$[D]=[R^{\ddagger}][T][T]^{-1}[C^{\ddagger}] \quad (2)$$

$$\overline{R}_l=[R^{\ddagger}]T_l\, \overline{C}_l=T_l'[C^{\ddagger}] \quad (3)$$

$$T_l=[\lambda^{\ddagger}]^{-1}[R^{\ddagger}]^T\overline{R}_l\, T_l'=\overline{C}_l[C^{\ddagger}]^T \quad (4)$$

Significantly, it is not necessary to identify the entire transformation matrix [T] because individual vectors can be identified one at a time. As shown in Equation 3, where $\overline{R}_l$ or $\overline{C}_l$ are predicted vectors and $T_l$ and $T_l'$ are $l^{th}$ column and row transformation vectors of [T] and $[T]^{-1}$ respectively. The transformation vectors can be found by Equation 4, where $[\lambda^{\ddagger}]$ is the diagonal matrix of eigenvalues corresponding to the retained principal components, and $\overline{R}_l$ or $\overline{C}_l$ are the test vectors. As mentioned above, the test vectors can comprise reference summed ion spectra contained in a reference library. Alternatively, however, the test vectors may be obtained from a library assembled from theoretical considerations, empirical knowledge, or intuition. It is common practice to organize [D] such that each row corresponds to an object (i.e., sample spectrum) and each column corresponds to a variable (i.e., wavelength). The test vectors will be spectra and the second equations in lines (3) and (4) may be preferred in some applications.

The test vector $\overline{C}_l$ and predicted vector $\overline{C}_l$ will show a high degree of similarity (i.e., Pearson product moment correlation approaching 1) if the test vector is a potentially significant contributor to the data set. Furthermore, when a given class of analyte contributes to a sample set, test and predicted vectors from that class should show higher similarities than those from non-contributing classes. The property of target factor analysis that allows the search for one transformation vector at a time can then be utilized to identify a class of analyte that may contribute to a data set, even in the presence of interferences.

After the comparisons have been made between the sample data and the reference substances, a determination as to the class to which the analyte belongs can be made. Classifiers can be described as "hard" and "soft" classifiers. Hard classifiers assign each sample to only one class, and each sample must be classified. Soft classifiers provide the additional options of assigning each sample to multiple classes or to not assign the sample to any of the available classes. Soft classifiers are more flexible and therefore may be considered more useful. Described below is implementation of the results of a target factor analysis as soft classifier. It is the combination of target factor analysis with the classification method described below that comprises what is referred to herein as target factor discriminant analysis (TFDA).

In a multi-class classification problem, it is common for each class ($\omega_i$) to be defined by one or more measurable parameters (i.e., x in a single parameter case). Following Bayesian decision theory, the posterior probability ($P(\omega_i|x)$ in Equation 5, that an object belongs to a given class can be assessed by the value of the measurable parameter x for that object, a probability density function $p(x|\omega_i)$, and the prior probabilities for encountering each class $P(\omega_i)$. The probability density function can be approximated in different ways, with assumptions of normality and the use of kernel functions constituting common approaches. If the prior probabilities are not known, it is common to assign them equal values or values proportional to the relative populations of each class. The posterior probability for membership in each class is calculated at x and class membership is assigned based on the largest probability.

$$P(\omega_i \mid x) = \frac{p(x \mid \omega_i) P(\omega_i)}{\sum_i p(x \mid \omega_i) P(\omega_i)} \quad (5)$$

In the application examined here, the probability density functions $p(r|\omega_i)$ change for each set of target factor analysis results where a library of spectra that may contribute to a data set has been examined and the correlation between $\overline{C}_j$ and $\overline{C}_l$ has been determined for all library members of each class. For example, if there are n classes, $\omega_1$-$\omega_n$, under consideration in a problem where $\omega_1$ contributes to the samples, then the distribution of r values for $\omega_1$ will tend to be larger than those for the remaining n-1 classes. However, in a problem where a different class contributes to the sample set, the distribution of r values for the contributing class will tend to be larger and the relative ordering of the distributions for the remaining classes will also change. It is therefore may be necessary to evaluate $p(r|\omega_i)$ following target factor analysis of each sample set. One method of estimating $p(r|\omega_i)$ involves using a kernel approximation given in Equation 6, which simulates each distribution by a superposition of normal distribution functions centered at each of the $n_i$ correlation values for each class $\omega_i$. In Equation 6, the value $h_i$ is equivalent to the standard deviation in the normal distribution.

$$p(r, \omega_i) = \frac{1}{n_i} \sum_{j=1}^{n_i} \frac{1}{h_i \sqrt{2\pi}} \exp\left[\frac{1}{2h_i^2}(r - r_j)^2\right] \quad (6)$$

Two further considerations are important to interpreting the results from the combined target factor analysis and Bayesian decision theory: (1) there may be cases where an analyte of interest makes an extremely weak contribution to the data set or is not present, and in that case the dataset should not be classified, and (2) it is important to determine the value of r where the posterior probability $P(\omega_i|r)$ will be calculated.

The coefficient of determination $r^2$ can be interpreted as the percentage of the variation in the predicted vector that is associated with variability in the test vector. Although an r (or $r^2$) of 1.0 is ideal, the correlations observed for real-world data may not approach unity. The value of r may serve as a criterion for determining if classification is appropriate. A conservative approach for determining the range where r is useful for classification is to limit the calculation of posterior probability to classes that have a median correlation $r_M$ that is close to unity, i.e., within five times the median absolute deviation for the class $r_{MAD}$. This approach only allows calculation of posterior probabilities for classes where there is greater than approximately 1% chance of observing r=1. In this approach, evaluation of $P(\omega_i|r)$ is made at r=1, which represents a perfect correlation between the test and predicted vectors. The posterior probability is set to zero for classes where $(1-r_M)/r_{MAD} > 5$. In the event that $(1-r_M)/r_{MAD} > 5$ for all classes, the sample is not classified.

As described to this point, TFDA can be used to assign a sample to a single class or provide a basis for not assigning the sample to any available class. The last step to make TFDA a soft classifier is to describe the methodology for assignment to two or more classes. When the distributions of correlation coefficients (or any similarity metric) are highly similar, it is possible that the sample should be assigned to two or more classes. Assignment to multiple classes is warranted when the distribution of correlation coefficients (or similarity metrics) for a given class is not significantly different from the distribution for the class having the highest calculated posterior probability. A statistical comparison of the medians for two distributions can be used to make this determination, and the comparison can be accomplished with the Wilcoxon rank sum test or other appropriate statistical test. If the two distributions cannot be distinguished at some pre-determined significance level based on the Wilcoxon rank sum test (or other appropriate test), then the sample should be assigned to both classes.

Figure 5A:
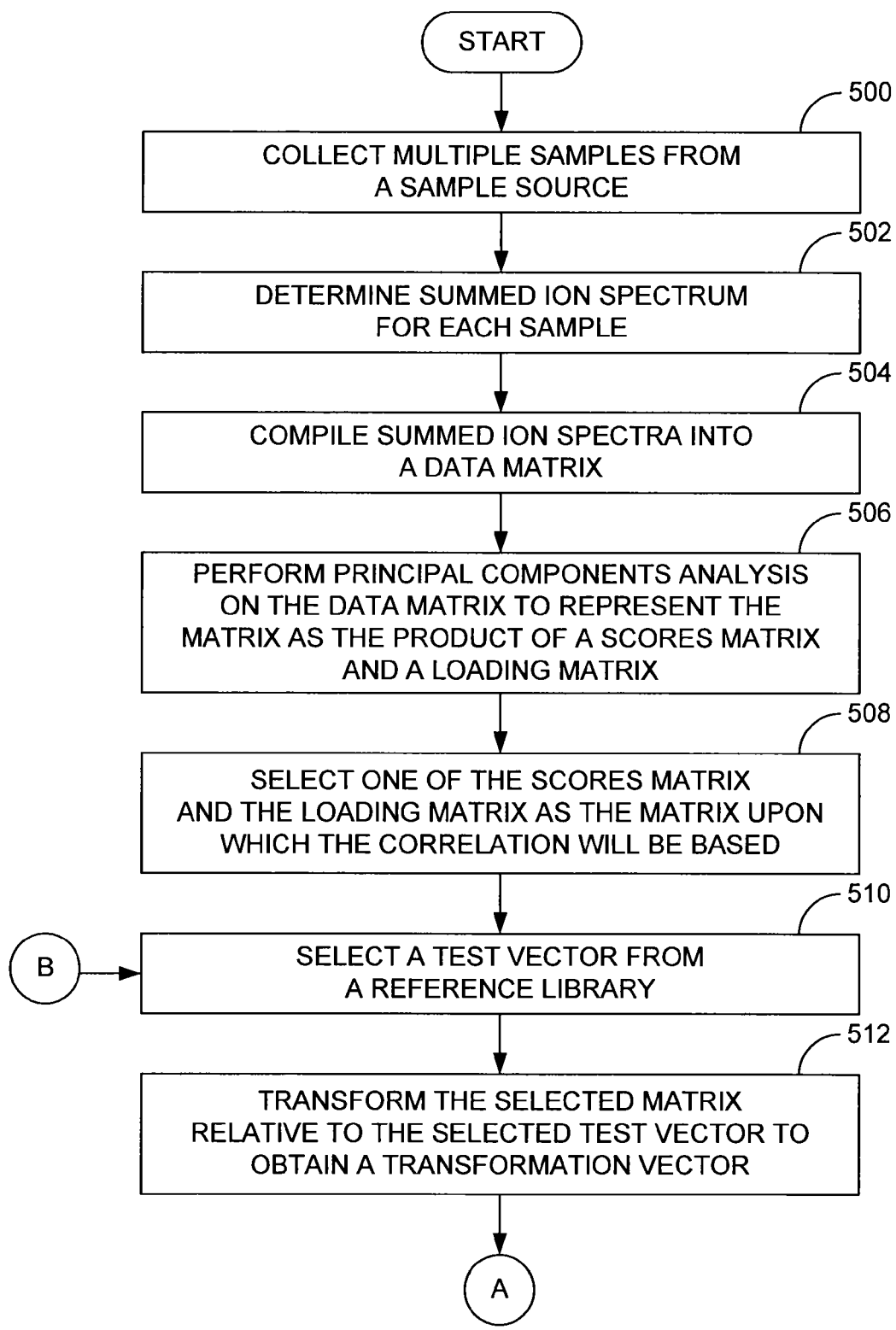
FIGS. 5A and 5B comprise a flow diagram of a second embodiment of a method for identifying a class of a component of a mixture.
Figure 5B:
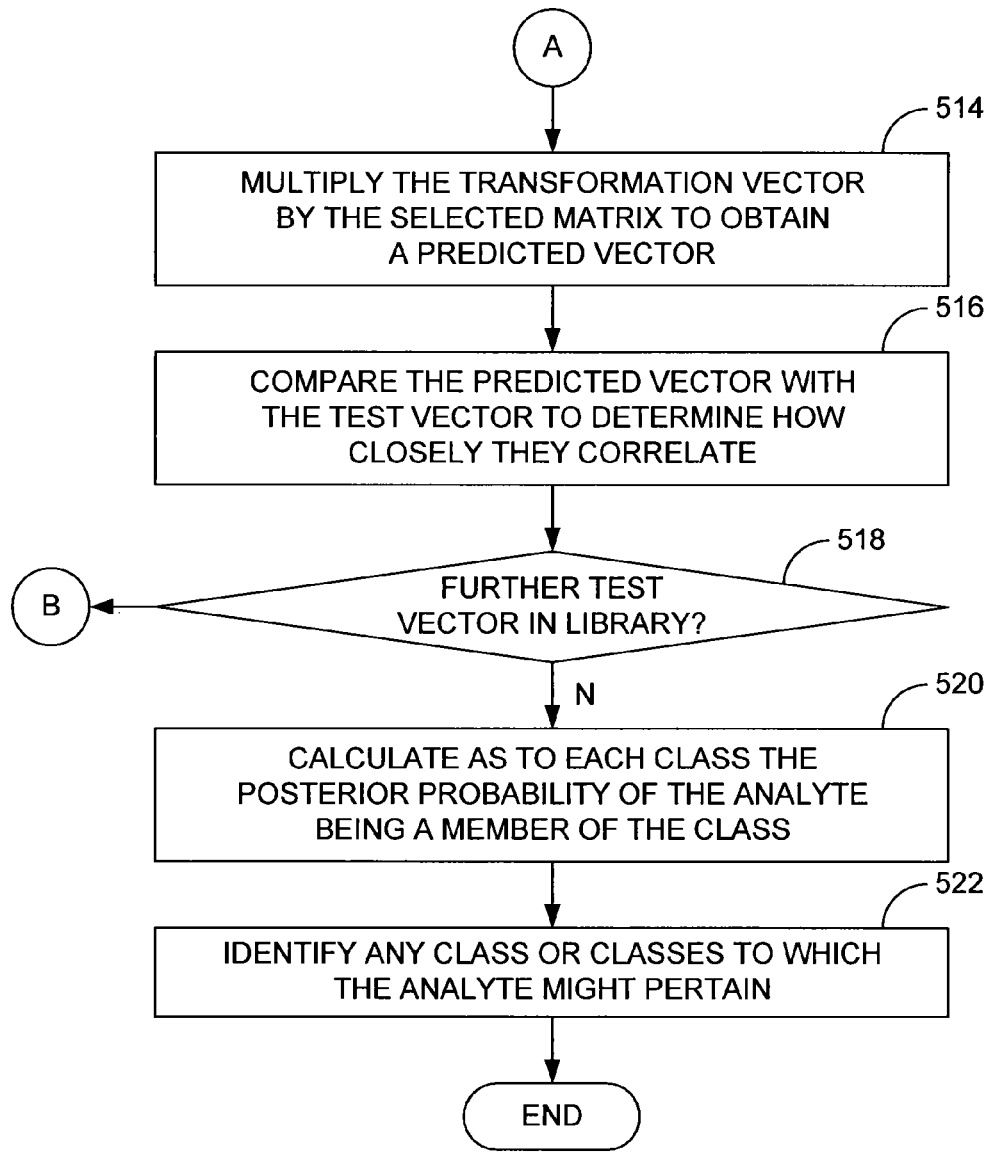

FIGS. 5A and 5B illustrate a second example method for identifying the class of a substance (component) contained in a material (mixture), which incorporates the target factor discriminant analysis described above. Beginning with block 500 of FIG. 5A, multiple samples are collected from a sample source and, as noted block 502, the summed ion spectrum are determined for each sample.

Once the summed ion spectra for the samples have been determined, the summed ion spectra, which are vectors comprising listings of intensities (numbers) at different mass-to-charge ratios, are compiled into a data matrix, as indicated in block 504. Next, principal components analysis is performed on the data matrix to represent the matrix as the product of a scores matrix ([$R^\ddagger$]) and loading matrix ([$C^\ddagger$]), as indicated in block 506. With reference to block 508, one of those matrices is selected as the matrix upon which the correlations will be based. In some embodiments, the loading matrix [$C^\ddagger$] is preferred for this purpose.

Referring next to block 510, a test vector is selected from a reference library. As described above, the library can comprise hundreds of summed ion spectra for various substances, such as ignitable liquids. Like the summed ion spectra of the test samples, each summed ion spectrum in the library is a vector comprising a listing of intensities at different mass-to-charge ratios. Once a test vector is selected, the selected matrix is transformed relative to the selected test vector to obtain a transformation vector, as indicated in block 512. An example of this action is shown in Equation 4 in which the test vector $\overline{C}_j$ is multiplied by the transform of the loading vector [$C^\ddagger$] (i.e., [$C^\ddagger$]$^T$) to obtain the transformation vector $T_j'$.

With reference next to block 514 of FIG. 5B, the transformation vector is multiplied by the selected matrix to obtain a predicted vector. An example of this action is shown in Equation 3 in which the predicted vector $\overline{C}_j$ is obtained by multiplying $T_j'$ by [$C^\ddagger$]. Once the predicted vector has been obtained, it can be compared to the associated test vector to determine how closely they correlate, as indicated in block 516. As described above, this action can produce a correlation coefficient that ranges from 0 to 1, with 1 being perfect correlation and 0 being no correlation.

From this point, flow depends upon whether there is another test vector in the library to which to compare, as indicated in decision block 518. If there is a least one more test vector, flow returns to block 510 of FIG. 5A, the next test vector is selected, and the correlation described above is performed again. Flow continues in this manner until each test vector has been compared to a predicted vector.

Once all the comparisons have been made, correlations (e.g., correlation coefficients) have been generated for each of the test vectors and therefore each substance of the library. As indicated in block 520, the posterior probability of the analyte in the samples being a member of a class is calculated as to each class in accordance with Bayesian decision theory. As described above, the posterior probability can optionally only be calculated for classes that have a median correlation that is within five times the median absolute deviation for the class. Once the probabilities have been determined for each class, any class or classes to which the analyte might pertain can be identified, as indicated in block 522. Because soft classification is used, one, multiple, or no classes can be identified.

The systems and methods disclosed above provide a decision tool that can be automated, if desired. The systems and methods can be applied to the interpretation of complex samples in a laboratory, interpretation of sensor data in laboratory or field-deployed instruments, and process and manufacturing control. Areas of application for the systems and methods include forensic science (complex mixture classification), medicine (disease or pathogen classification), security applications (threat classification), and the like.

We claim:

1. A method for identifying a class of a component of a mixture, the method comprising:
   collecting samples of the mixture from a sample source;
   determining a summed ion spectrum for each sample and generating sample data from the summed ion spectra;
   comparing the sample data with reference summed ion spectra of multiple reference substances to determine correlations between the reference substances and the sample data, each reference substance belonging to a particular substance class; and
   evaluating the correlations of each substance class to determine which substance class most closely correlates to the sample data.

2. The method of claim 1, wherein collecting samples comprises collecting debris from a scene of a fire or an explosion.

3. The method of claim 1, wherein the summed ion spectra comprise intensities at different mass-to-charge ratios.

4. The method of claim 1, wherein comparing the sample data with the reference summed ion spectra comprises performing target factor analysis.

5. The method of claim 4, wherein performing target factor analysis comprises compiling the summed ion spectra of the collected samples into a data matrix and performing principal components analysis on the data matrix to represent the data matrix as the product of a scores matrix and a loading matrix.

6. The method of claim 5, wherein the reference summed ion spectra are test vectors and performing target factor analysis further comprises selecting one of the scores matrix and a loading matrix and separately transforming the selected matrix relative to each test vector to obtain a transformation vector for each test vector.

7. The method of claim 6, wherein performing target factor analysis further comprises individually multiplying the transformation vectors and the selected matrix to obtain an associated predicted vector for each test vector and comparing the test vector with its associated predicted vector to determine how closely they correlate.

8. The method of claim 1, wherein sets of correlations are obtained from the comparisons, one set for each substance class, and wherein determining which substance class most closely correlates to the sample data comprises determining which set of correlations correlates most closely to the sample data using Bayesian decision theory.

9. The method of claim 8, wherein determining which set of correlations correlates most closely to the sample data is performed using soft classification such that a solution to the classification problem can be one class, multiple classes, or no classes of substances.

10. The method of claim 8, wherein determining which set of correlations correlates most closely to the sample data comprises calculating as to each substance class a posterior probability of the component of the mixture being a member of the class.

11. The method of claim 10, further comprising selecting substance classes having median correlations within five times a median absolute deviation from a value of one before calculating the posterior probability.

12. A system for identifying a class of a component of a mixture, the system comprising:
    a processing device; and
    memory that stores a substance classification system configured to:
      obtain sample data associated with summed ion spectra of samples of the mixture,
      compare the sample data with reference summed ion spectra of multiple reference substances to determine correlations between the reference substances and the sample data, each reference substance belonging to a particular substance class, and
      evaluate the correlations of the substances of each substance class to determine which substance class most closely correlates to the sample data.

13. The system of claim 12, wherein the substance classification system is configured to compare the sample data with the reference summed ion spectra by performing target factor analysis.

14. The system of claim 13, wherein performing target factor analysis comprises compiling the summed ion spectra of the collected samples into a data matrix and performing principal components analysis on the data matrix to represent the data matrix as the product of a scores matrix and a loading matrix.

15. The system of claim 14, wherein the reference summed ion spectra are test vectors and performing target factor analysis further comprises selecting one of the scores matrix and a loading matrix and separately transforming the selected matrix relative to each test vector to obtain a transformation vector for each test vector.

16. The system of claim 15, wherein performing target factor analysis further comprises individually multiplying the transformation vectors and the selected matrix to obtain an associated predicted vector for each test vector and comparing the test vector with its associated predicted vector to determine how closely they correlate.

17. The system of claim 12, wherein sets of correlations are obtained from the comparisons, one set for each substance class, and wherein the substance classification system determines which substance class most closely correlates to the sample data by determining which set of correlations correlates most closely to the sample data using Bayesian decision theory.

18. The system of claim 17, wherein determining which set of correlations correlates most closely to the sample data is performed using soft classification such that a solution to the classification problem can be one class, multiple classes, or no classes of substances.

19. The system of claim 17, wherein determining which set of correlations correlates most closely to the sample data comprises calculating as to each substance class a posterior probability of the component of the mixture being a member of the class.

20. The system of claim 19, further comprising selecting substance classes having median correlations within five times a median absolute deviation from a value of one before calculating the posterior probability.

21. A computer-readable medium that stores a substance classification system, the substance classification system comprising:

logic configured to obtain sample data associated with summed ion spectra of samples of the mixture;

logic configured to compare the sample data with reference summed ion spectra of multiple reference substances to determine correlations between the reference substances and the sample data, each reference substance belonging to a particular substance class; and logic configured to evaluate the correlations of the substances of each substance class to determine which substance class most closely correlates to the sample data.

22. The computer-readable medium of claim 21, wherein the logic configured to compare is configured to compare the sample data with the reference summed ion spectra by performing target factor analysis.

23. The computer-readable medium of claim 22, wherein performing target factor analysis comprises compiling the summed ion spectra of the collected samples into a data matrix and performing principal components analysis on the data matrix to represent the data matrix as the product of a scores matrix and a loading matrix.

24. The computer-readable medium of claim 23, wherein the reference summed ion spectra are test vectors and performing target factor analysis further comprises selecting one of the scores matrix and a loading matrix and separately transforming the selected matrix relative to each test vector to obtain a transformation vector for each test vector.

25. The computer-readable medium of claim 24, wherein performing target factor analysis further comprises individually multiplying the transformation vectors and the selected matrix to obtain an associated predicted vector for each test vector and comparing the test vector with its associated predicted vector to determine how closely they correlate.

26. The computer-readable medium of claim 21, wherein sets of correlations are obtained from the comparisons, one for each substance class, and wherein the logic configured to evaluate is configured to determine which substance class most closely correlates to the sample data by determining which set of correlations associated with the classes correlates most closely to the sample data using Bayesian decision theory.

27. The computer-readable medium of claim 26, wherein determining which set of correlations correlates most closely to the sample data is performed using soft classification such that a solution to the classification problem can be one class, multiple classes, or no classes of substances.

28. The computer-readable medium of claim 26, wherein determining which set of correlations correlates most closely to the sample data comprises calculating as to each set substance class a posterior probability of the component of the mixture being a member of the class.

29. The computer-readable medium of claim 28, wherein the logic configured to evaluate is further configured to select substance classes having median correlations within five times a median absolute deviation from a value of one before calculating the posterior probability.

* * * * *